United States Patent [19]

Hanson

[11] Patent Number: 4,560,923
[45] Date of Patent: Dec. 24, 1985

[54] MOISTURE ANALYZER

[76] Inventor: Colin J. Hanson, 22719 Rio Reyes Ct., Valencia, Calif. 91355

[21] Appl. No.: 551,846

[22] Filed: Nov. 15, 1983

[51] Int. Cl.$^4$ .......................................... G01R 27/26
[52] U.S. Cl. .............................................. 324/61 QL
[58] Field of Search .............. 324/61 R, 61 QL, 61 P, 324/59; 340/602

[56] References Cited

U.S. PATENT DOCUMENTS

| 3,443,219 | 5/1969 | Adams | 324/61 R |
| 3,723,865 | 3/1973 | Batey et al. | 324/61 R |
| 4,468,610 | 9/1984 | Hanson | 324/61 R |

Primary Examiner—Stanley T. Krawczewicz
Assistant Examiner—Jack B. Harvey
Attorney, Agent, or Firm—John E. Toupal; Harold G. Jarcho

[57] ABSTRACT

A moisture analyzing system including an antenna coupled to a frequency-modulated voltage source and arranged to apply an alternating electric field to a material being tested for moisture content. An LC tank circuit is connected in parallel with the antenna and a resistance is connected between the source and the parallel combination of the antenna and the tank circuit. Detecting the level of resonant voltage peak output signals produced across the tank circuit is a measurement circuit which provides therewith a sensing signal indicative of the moisture content of the material being tested. The detection of resonant peak amplitudes produced by frequency sweeping a tank circuit eliminates many unstable variables that interfere with moisture measurements.

20 Claims, 9 Drawing Figures

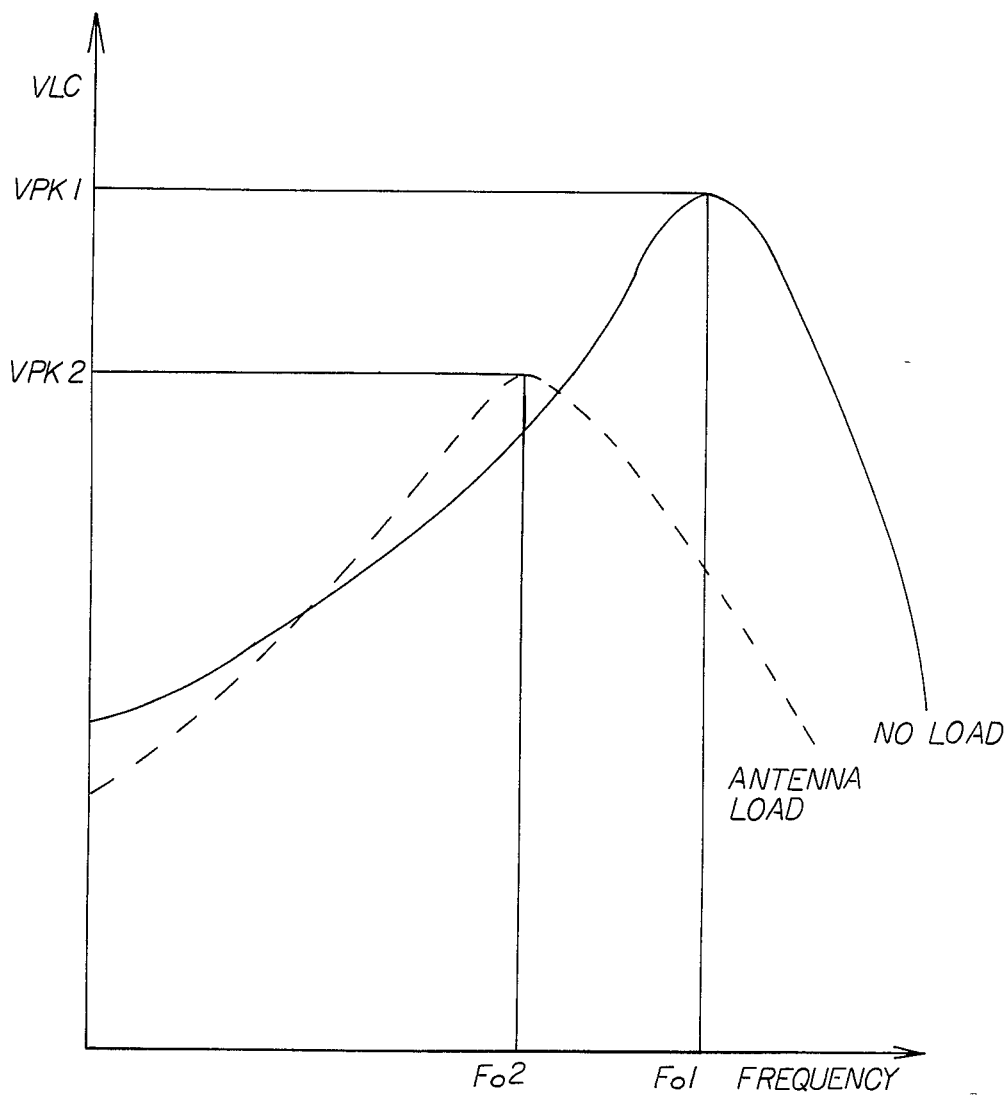
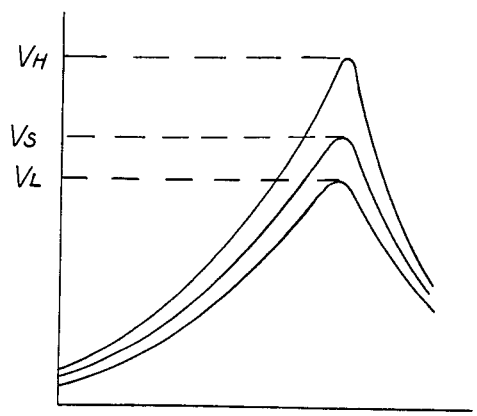
FIG.5
FIG.6

MOISTURE ANALYZER

BACKGROUND OF THE INVENTION

This invention relates generally to a moisture analyzing system and, more particularly to a non-contacting radio frequency system for making continuous on-line moisture measurements.

Various types of moisture analyzing systems apply a high frequency electric field to a material under test. While the electric field is being applied, changes in some electrical characteristic are detected and measured to determine moisture content of the material. Included in such systems are those which measure changes in capacitance. Examples of capacitive measuring systems are disclosed in U.S. Pat. Nos. 3,793,595 and 4,259,632. Other systems measure electromagnetic or microwave energy loss within the material. Examples of energy loss measuring systems are disclosed in U.S. Pat. Nos. 3,981,082 and 4,193,027. Still other systems measure frequency change in the applied field, An example of a frequency change measurement system is disclosed in U.S. Pat. No. 3,684,952.

Although providing measurements indicative of moisture content, the above noted prior systems suffer from a number of individual and collective deficiencies. Typical disadvantages of conventional moisture measurement systems are excessive cost, inability to perform on-line measurements, limited accuracy, ambient temperature sensitivity, sensitivity to product density and shape, inability to function in harsh environments, etc.

The object of this invention, therefore, is to provide an improved moisture analyzing system that will alleviate problems associated with prior alternating electric field measurement systems.

SUMMARY OF THE INVENTION

The invention is a moisture analyzing system including an antenna coupled to a frequency-modulated voltage source and arranged to apply an alternating electric field to a material being tested for moisture content. An LC tank circuit is connected in parallel with the antenna and a resistance is connected between the source and the parallel combination of the antenna and the tank circuit. Detecting the level of resonant voltage peak output signals $V_O$ produced across the tank circuit is a measurement circuit that provides therewith a sensing signal $V_S$ indicative of the moisture content of the material being tested. The detection of resonant peak amplitudes produced by frequency sweeping a tank circuit eliminates many unstable variables that interfere with moisture measurements.

According to one feature of the invention the system includes a high reference means producing a high voltage reference signal $V_H$, a low reference means producing a low voltage reference signal $V_L$ and the measurement circuit comprises a processing circuit providing a moisture indicating compensated output signal proportional to $(V_S-V_L)/(V_H-V_L)$. The resultant ratio signal eliminates inaccuracies that can result from circuit instability.

According to other features of the invention the system includes a material feed mechanism for feeding the material through the alternating electric field, the frequency modulated source comprises a sweep generator and a variable frequency oscillator driven thereby, and the antenna comprises spaced apart planar electrodes providing an electric field through which the material is fed. This arrangement facilitates use of the system for continuous on-line measurements.

According to yet other features of the invention, the reference means comprise a high reference impedance; a low reference impedance; timing means; and switching means responsive to the timing means to maintain the antenna in parallel with the tank circuit during sensing periods during which the output signal $V_O$ comprises the moisture sensing signal $V_S$, to substitute the high reference impedance for the antenna during high reference periods during which the output signal $V_O$ comprises the high reference signal $V_H$, and to substitute the low reference impedance for the antenna during low reference periods during which the output signal $V_O$ comprises the low reference signal $V_L$. This arrangement provides the desired reference signals in an efficient and easily implemented manner.

According to still other features of the invention, the processing circuit comprises isolation means responsive to the timing means for isolating from the output signal $V_O$ the sensing signal $V_S$, the high reference signal $V_H$, and the low reference signal $V_L$; and the high reference impedance comprises a capacitor, and the low reference impedance comprises a resistor. The high and low impedances alter the resonant frequency of the tank circuit to provide the desired reference signals and the isolation thereof facilitates generation of the desired ratio output signal.

According to additional features of the invention, the processing means further comprises low reference sampling means responsive to the timing means and operative during low reference sampling periods to sample and hold values of the output signal $V_O$ produced during the low reference periods, subtraction circuit means producing a difference signal dependent on the values of $(V_O-V_L)$, high reference sampling means responsive to the timing means and operative during high reference sampling periods to sample and hold values of the difference signals $(V_O-V_L)$ produced during the high reference periods, divider circuit means producing a ratio signal dependent on the ratios of said difference signals and the signals stored by the high reference sampling means, and distinguishing circuit means responsive to the timing means and producing from the ratio signals the compensated signal $(V_S-V_L)/(V_H-V_L)$ only during sampling portions of the sensing periods. This arrangement facilitates the desired isolation of the sensing and reference signals.

According to a further feature of the invention, the low reference sampling periods are shorter than and substantially time centered with respect to the low reference periods, the high reference sampling periods are shorter than and substantially time centered with respect to the high reference periods, and the sampling portions are shorter than and substantially time centered with respect to the sensing periods. The provision of shortened, centered sampling periods enhances the stability of the system.

According to one other feature of the invention, the timing and switching means are operative to produce between the sensing and high reference periods first combined periods during which both the antenna and the high reference impedance are connected in parallel with the tank circuit, and to produce between the sensing and low reference periods second combined periods during which both the antenna and the low reference impedance are connected in parallel with the tank circuit. The provision of combined periods improves stability of the system by ensuring continuity of the output signal $V_O$.

DESCRIPTION OF THE DRAWINGS

These and other objects and features of the invention will become more apparent upon a perusal of the following description taken in conjunction with the accompanying drawings wherein:

FIG. 5 is a waveform relating to operation of the system in FIG. 1;

FIG. 6 is a diagram showing different waveforms generated in the system of FIG. 1;

DESCRIPTION OF THE PREFERRED EMBODIMENT

Figure 1:
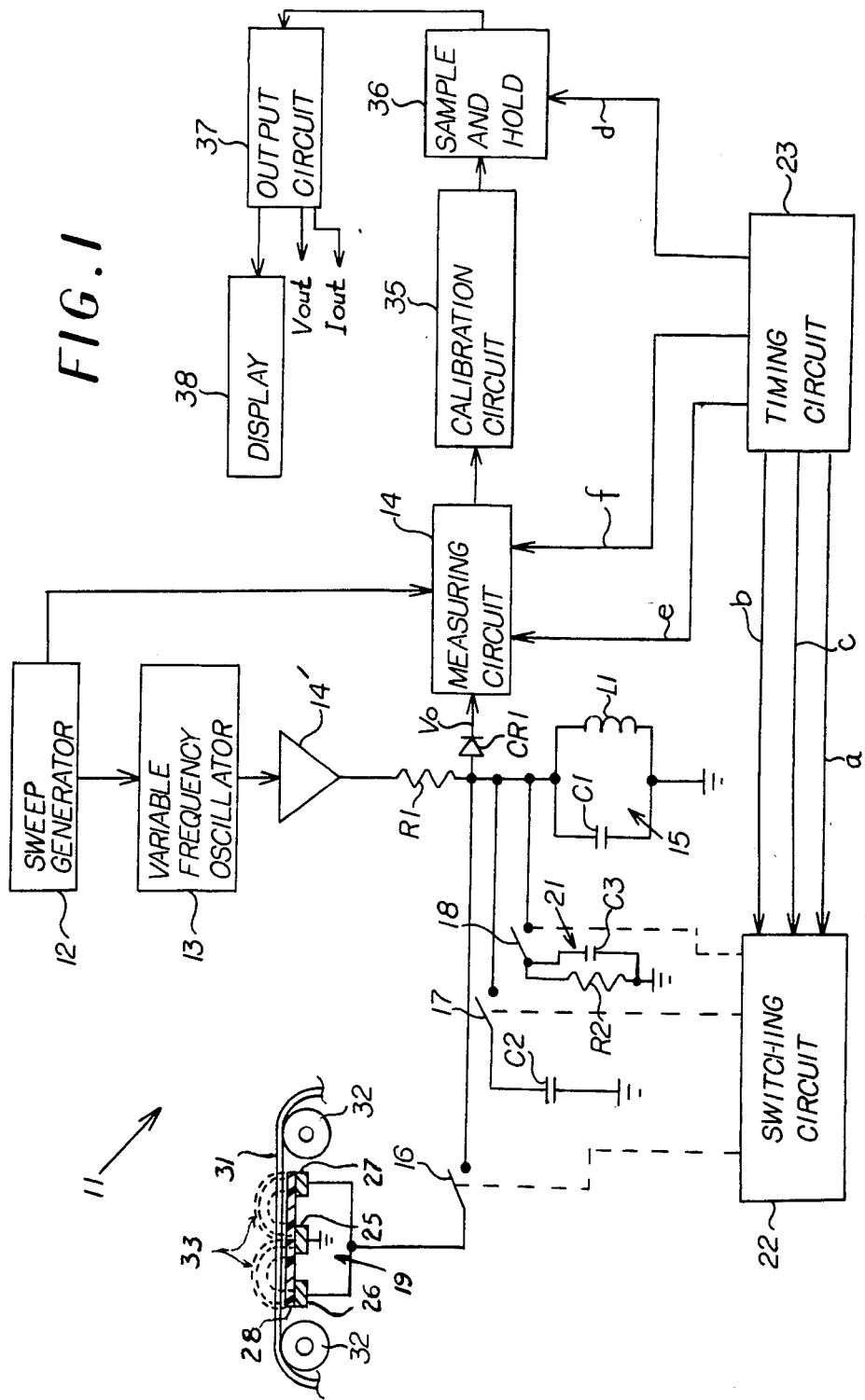
FIG. 1 is a schematic block diagram illustrating a moisture analyzing system of the invention.

Referring now to FIG. 1 there is shown in block diagram form a moisture sensing system 11 in accordance with the invention. A sweep generator 12 supplies a sawtooth modulating waveform to a variable frequency oscillator 13 and a synchronized square wave to a measuring circuit 14. The output of the oscillator 13 is therefore frequency modulated, and is amplified by an amplifier 14' before being applied to a series combination of a load resistor R1 and a tank circuit 15 comprising a parallel combination of a capacitor C1 and an inductor L1. The voltage appearing between the load resistor R1 and the tank circuit 15 is detected by a detector diode CR1 that supplies a detected output voltage $V_O$ to the measuring circuit 14. Also connected to the junction between the load resistor R1 and the tank circuit 15 by contacts 16, 17 and 18, respectively, are an antenna 19, a high reference impedance capacitor C2, and a low reference impedance 21 consisting of a parallel connected capacitor C3 and a resistor R2. As described hereinafter, the contacts 16, 17 and 18 are activated by a switching circuit 22 that is controlled by a timing circuit 23.

The antenna 19 consists of a grounded planar electrode 25 straddled by and spaced from planar electrodes 26, 27, all supported on an insulator substrate 28. Passing directly above the substrate 28 is a sheet of material 31 that is conveyed by rollers 32 of a conventional feed mechanism (not shown). With the electrodes 26, 27 connected by the switch 16 to the output of the oscillator 13, the antenna 19 produces an alternating electric field with field lines 33 that twice pass through the material 31, as shown.

As also described below in greater detail, the measuring circuit 14 responds to signals received from the timing circuit 23 by processing the output signal $V_O$ to produce processed signals indicative of the moisture content of the material 31. After passing through a conventional calibration circuit 35 those signals are sampled and held by a conventional sample and hold circuit 36 also receiving an input from the timing circuit 23. The sample and hold circuit 36 supplies an output circuit 37 that produces outputs V out and I out indicative of the measured moisture content. Also receiving the output of the output circuit 37 is a moisture indicating display 38.

Figure 2:
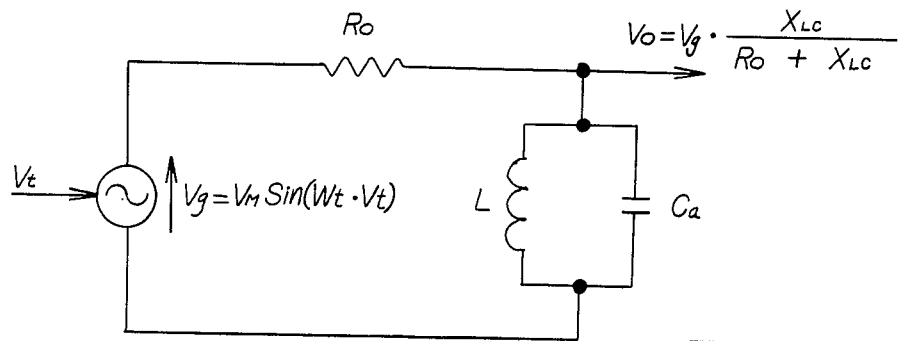
FIGS. 2–4 are electrical equivalent circuits clarifying certain operational characteristics of the system shown in FIG. 1.
Figure 3:
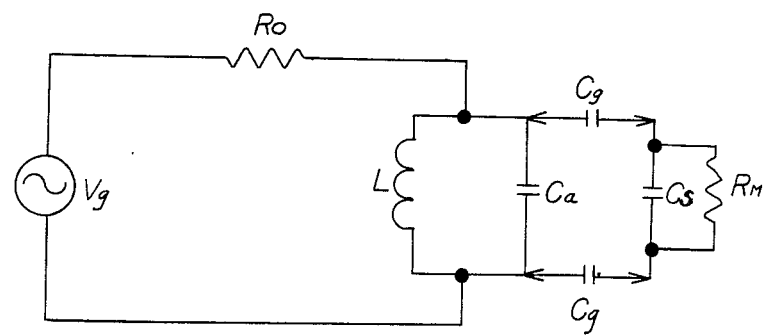
Figure 4:
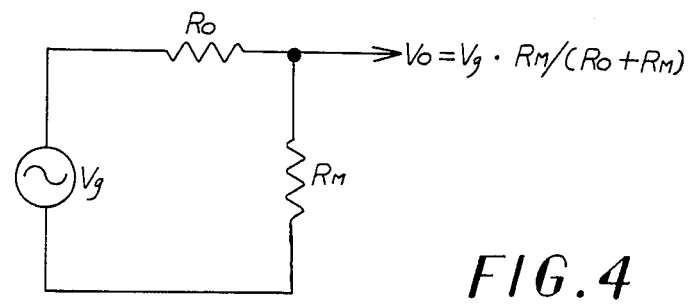

The operation of the antenna 19 is better understood by referring to the equivalent circuits shown in FIGS. 2–4. In the absence of a load material 31, the antenna 19 behaves electrically as a pure capacitor $C_a$, its dielectric being air. With the antenna 19 connected in parallel with a pure inductance, a resonant circuit results, the natural frequency of which is: $F_O = 1/(2\pi\sqrt{LC})$. By energizing such a circuit with a frequency modulated source as in FIG. 2, the center frequency being approximately $F_O$, there will be produced an output $V_O = V_G X_{LC}/R_O + X_{LC}$ where $X_{LC}$ = tank circuit reactance = $jwL/(1-w^2LC)$. Thus, the output signal $V_O$ will be a FM waveform, the amplitude being modulated by a series of resonant peaks. With a pure LC tuned circuit, the impedance at resonance will be infinite, and the peak output in FIG. 2 therefore will be $V_M$.

If the sample material 31 is now introduced into the electric field 33 produced by the antenna 19, the field will distort due to a change in dielectric. Consequently, the apparent capacitance will increase since a solid material will certainly have a higher dielectric permittivity than air. In addition, chemical compounds when in aqueous solution, dissociate to form electrically charged ions. Those ions behave in many ways as free electrons would in a metallic conductor; i.e. when an electric potential is applied to the solution, the negative ions will be attracted to the positive electrode (anode) and the positive ions will be attracted to the negative electrode (cathode) producing a current flow, ionic conductance. Since most naturally occurring water has a mineral content and, therefore, a certain number of free ions, the number of ions in a given source will be directly proportional to volume of water. Therefore, the material 31 almost certainly will exhibit a loss factor or resistive element due to free ions inherent in its moisture content. As shown in FIG. 3, the sample material load 31 may be considered a capacitance $C_S$ in parallel with a resistance $R_M$. This parallel circuit is capacitively coupled to the original tank circuit by an airgap capacitance $C_g$. By lumping components, the entire circuit may be reduced to a parallel LCR network. FIG. 4 shows the circuit at resonance, when all reactive components cancel and the LCR network becomes purely resistive providing an output voltage $V_O = V_g R_M/(R_O + R_M)$.

Thus, as shown in FIG. 5 the amount of resistive (conductive) load on the antenna 19 is determined by the moisture content of the material 31 and is reflected entirely by the peak VPK2 of the resonant curve produced across the tank circuit 15. Given a highly stable signal source, and constant ambient conditions, it would be possible, therefore, to measure the peak VPK2 and equate it to moisture content of the material 31. However, conditions are seldom ideal and extreme circuit stability can be obtained only at excessive cost. These problems are eliminated in the measurement system 11 by the dual reference switching system shown in FIG. 1.

At predetermined intervals, the antenna 19 is switched out of the circuit 11 and either the high reference impedance C2 or the low reference impedance 21 is switched into the circuit. For each sequential load, the tuned circuit 15 is swept through resonance providing as the output voltage $V_O$ three distinct peak readings. As illustrated in FIG. 6, the sequentially produced peak readings are the antenna produced peak $V_S$, the high reference impedance produced peak $V_H$ and the low reference impedance produced peak $V_L$. The algorithm to determine moisture content of the material 31 from the detected peak signals is; $(V_S-V_L)/(V_H-V_L)$. Eliminated by that measurement ratio are the two major sources of drift in the measurement circuit; i.e. output amplitude variation of the oscillator 13 due to aging and ambient temperature, and voltage drop of the detector diode CR1 caused by changes in ambient temperature. Oscillator amplitude variations will affect all three components of the measurement equation proportionately and will therefore ratio out while the subtraction of $V_L$ from both numerator and denominator portions of the ratio eliminate the effects of temperature induced changes in detector diode voltage drops.

Figure 7:
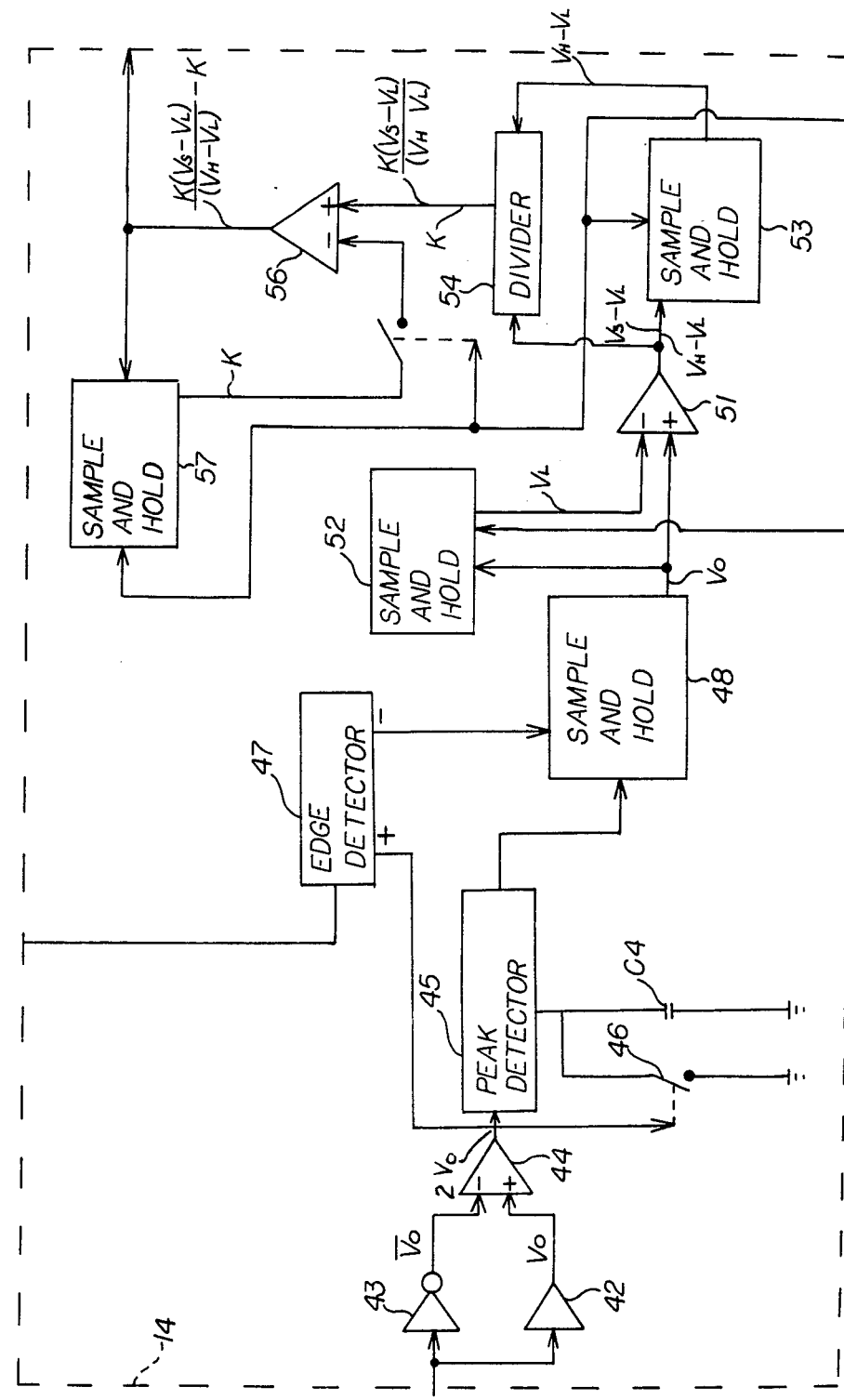
FIG. 7 is a schematic block diagram showing further details of the measuring circuit shown in FIG. 1.

Referring now to FIG. 7 there is shown in schematic block diagram form the measuring circuit 14 shown in FIG. 1. The detector diode CR1 applies the detected peak output signals $V_O$ to noninverting amplifier 42 and an inverting amplifier 43. Receiving the outputs $V_O$, $\overline{V_O}$, respectively, of the amplifiers 42, 43 is a differential amplifier 44 that produces an output $2V_O$. Preferably the signals $V_O$ and $\overline{V_O}$ are transmitted through twisted pair from identical source impedances such that any noise picked up by the connecting cable are the same for both signals. Thus, noise is eliminated from the $2V_O$ output of the differential amplifier 44.

A peak detector circuit 45 receives the $2V_O$ output of the differential amplifier 44 and includes a peak storage capacitor C4 that is charged to a voltage level determined by the amplitude of the input signal $2V_O$. Connected in parallel with the storage capacitor C4 are contacts 46 that are controlled by one output of an edge detector circuit 47. The output of the peak detector circuit 45 is sampled and held by a circuit 48 controlled by a second output signals from the edge detector circuit 47.

Controlling the output signals of the edge detector 47 is a square wave input provided by the sweep generator 12 shown in FIG. 1. The output of the sample and hold circuit 48 is applied to both one input of a differential amplifier 51 and a sample and hold circuit 52 that receives a low reference sampling signal from the timing circuit 23 shown in FIG. 1. Receiving the output of the sample and hold circuit 52 is the other input of the differential amplifier 51 that provides an output for both a sample and hold circuit 53 and a divider circuit 54. A high reference sample signal from the timing circuit 23 controls the sample and hold circuit 53 that provides a second input to the divider circuit 54. A differential amplifier 56 receives as one input the output from the divider 54 and provides an output that is sampled and held by a circuit 57. Also receiving the output of the differential amplifier 56 is the calibration circuit 35 shown in FIG. 1. The high reference sampling signal from the timing circuit 23 controls both the sample and hold circuit 57 and contacts 58 connected between the sample and hold circuit 57 and the other input of the differential amplifier 56.

OPERATION

Figure 8:
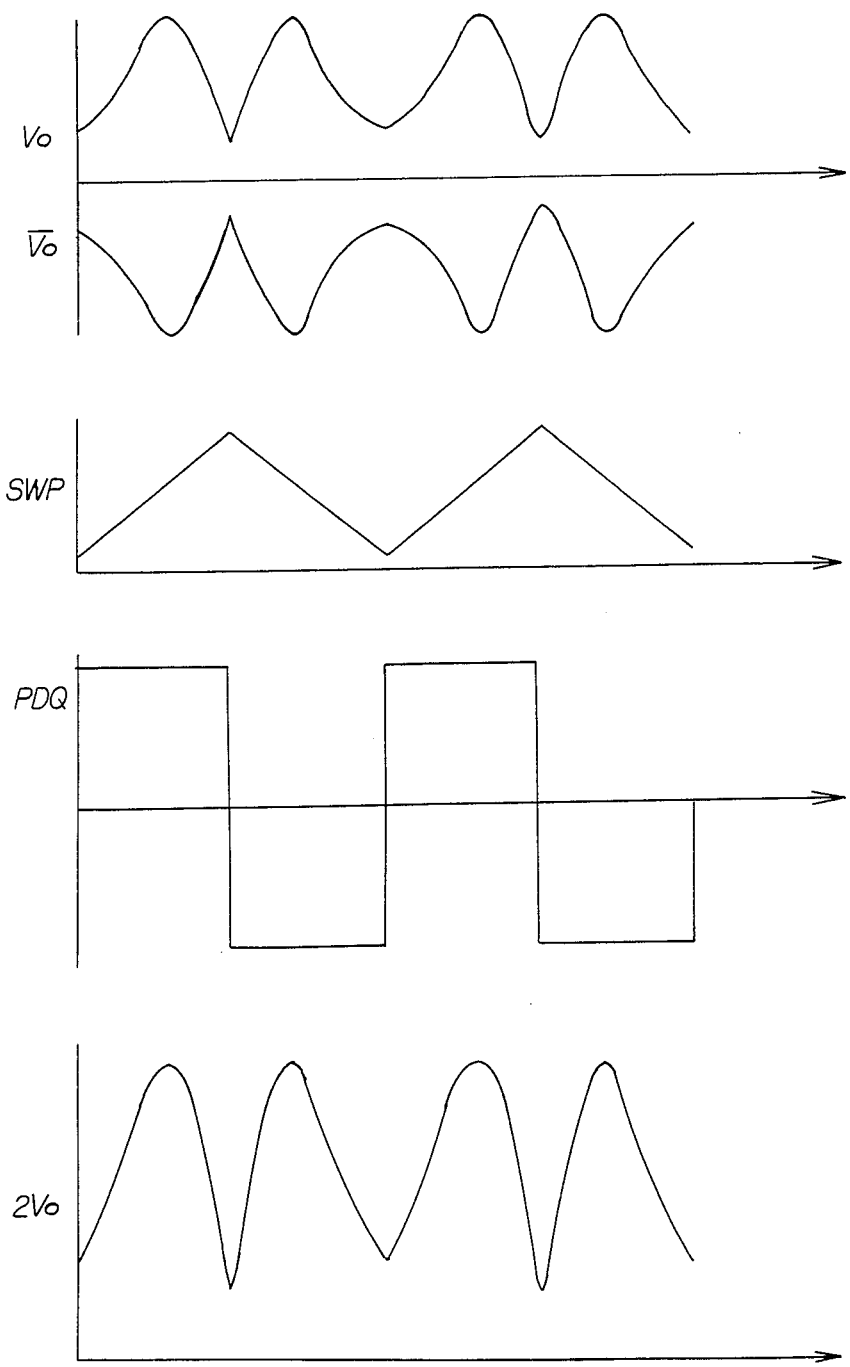
FIGS. 8 and 9 are diagrams showing various waveforms generated in the system shown in FIG. 1.

The operation of the measuring system 11 will now be described in conjunction with FIGS. 8 and 9, each of which illustrate time related waveforms generated by the sweep generator 12, the measuring circuit 14, and the timing circuit 23. As described above, the sweep generator 12 produces both a sawtooth modulating waveform SWP and a synchronized peak detect quenching square wave PDQ as shown in FIG. 8. In response to the sweep signal SWP, the variable frequency oscillator 13 produces an FM output, for example between 3.0-3.5 MHz that is amplified by the amplifier 14 and drives the tank circuit 15 via the fixed load resistor R1. Resonant peak amplitudes produced across the tank circuit 15 are detected by the detector diode CR1 and applied to the amplifiers 42, 43 (FIG. 7) resulting in the waveforms $V_O$ and $\overline{V_O}$ shown in FIG. 8. Subtraction in the amplifier 44 results in the waveform $2V_O$, the peak amplitudes of which are detected by the peak detector circuit 45. Each rising edge of the square wave signal PDQ produces from the edge detector 47 an output that closes the contacts 46 to discharge the peak storage capacitor C4. Thus, the storage capacitor C4 is discharged at the beginning of each sweep cycle provided by the sweep signal SWP. Each negative edge of the square wave signal PDQ triggers the edge detector 47 to produce an output that places the circuit 48 in a sample mode to store the output of the peak detector 45. Thus, the output of the sample and hold circuit 48 is a signal proportional to $V_O$ and indicative of the peak voltages produced by the tank circuit 15.

As illustrated by FIG. 6, the specific composition of the output $V_O$ is dependent upon the load that is switched in parallel with the tank circuit 15 by the switching circuit 22 (FIG. 1). Controlling the switching operation is the timing circuit 23 that provides timing signals shown in FIG. 9. Those signals include an antenna load timing signal a, a low reference timing signal b, and a high reference timing signal c all of which are applied to the switching circuit 22. In response to positive portions of the waveform a, the switching circuit 22 closes switch contacts 16 to connect the antenna 19 in parallel with the tank circuit 15. Similarly, positive portions of the waveform b cause the switching circuit 22 to close the contacts 18 connecting the low reference impedance 21 in parallel with the tank circuit 15 while positive portions of the waveform c cause the switching circuit 22 to close the contacts 17 connecting the high reference impedance C2 in parallel with the tank circuit 15.

Figure 9:
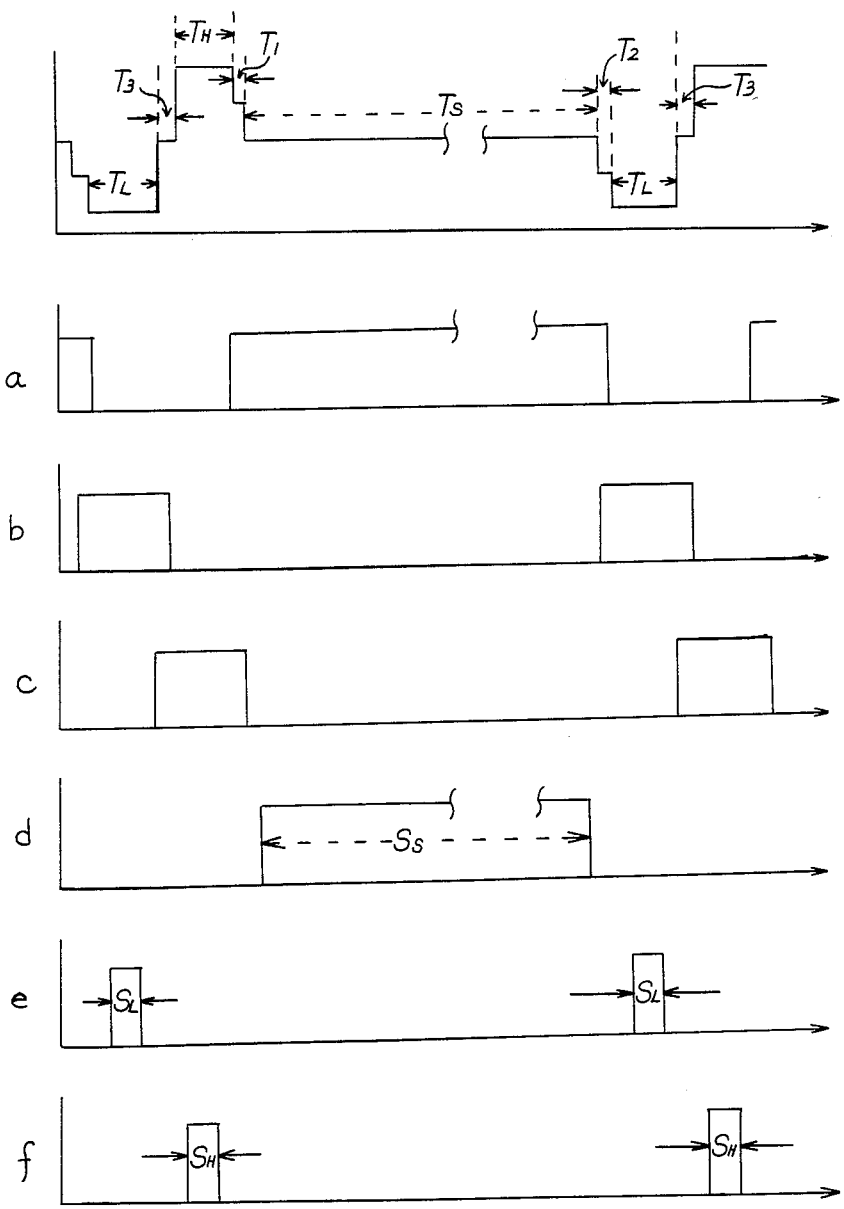

As a result of the above described switching operations, the signal voltage output $V_O$ of the sample and hold circuit 48 (FIG. 7) is a multi-level signal having distinct portions $V_S$, $V_L$ and $V_H$ depicted in FIG. 9. The signal portion $V_S$ is produced during a sensing period $T_S$ when only the antenna 19 is in parallel with the tank circuit 15. The signal portion $V_L$ is produced during a low reference timing period $T_L$ when only the low reference impedance 21 is parallel with the tank circuit 15 and the signal portion $V_H$ is produced during a high reference timing period $T_H$ when only the high reference impedance C2 is in parallel with the tank circuit 15. Preferably, the low reference and high reference timing periods $T_L$ and $T_H$ are substantially shorter than the sensing periods $T_S$, for example, 100 milliseconds for each reference period versus 3 seconds for the sensing periods. In that way a larger portion of moisture data is obtained while the relatively short periods $T_L$ and $T_H$ provide adequate reference data to compensate for circuit changes that are relatively long term.

As also shown by the waveforms in FIG. 9, the switching operations produce in addition to the timing periods $T_S$, $T_L$ and $T_H$ first combined timing periods $T_1$ during which both the antenna 19 and the high reference impedance C2 are connected in parallel with a tank circuit 15, second combined timing periods $T_2$ during which both the antenna 19 and the low reference impedance 21 are connected in parallel with the tank circuit 15 and third combined timing periods $T_3$ during which both the high reference impedance $C_2$ and the low reference impedance 21 are connected in parallel with the tank circuit 15. The combined timing periods $T_1$, $T_2$ and $T_3$ provide greater system stability by ensuring continuity of the output voltage $V_O$.

The measuring circuit 14 includes isolation circuitry for separating the composite output signal $V_O$ into the individual signal portions $V_S$ and $V_L$ and $V_H$ thereof. Again referring to FIG. 7, the circuit 52 samples and holds the output voltage $V_O$ during low reference sampling periods $S_L$ produced by positive portions of a waveform e (FIG. 9) received from the timing circuit 23. The low reference sampling periods $S_L$ are shorter and time centered with respect to the low reference timing periods $T_L$. Thus the output of the sample and hold circuit 52 comprises only the low reference signal portion $V_L$ of the output voltage $V_O$. After subtraction of the low reference signal $V_L$ from the output signal voltage $V_O$ in the differential amplifier 51, the resultant outputs are sequential signal periods comprising $V_S - V_L$ and signal periods comprising $V_H - V_L$.

The circuit 53 samples and holds the output of the amplifier 51 only during high reference sampling periods $S_H$ produced by positive portions of a waveform f received from the timing circuit 23. Those high reference sampling periods $S_H$ are shorter and time centered with respect to the high reference timing periods $T_H$. Thus, the output of the sample and hold circuit 53 is a signal $V_H - V_L$ that is applied to the highly linear multiplier-divider circuit 54. Produced by the divider circuit 54 during the sensing periods $T_S$ is a signal K $(V_S - V_L)/(V_H - V_L)$ where K is a circuit multiplier constant. The output of the divider circuit 54 is a signal K $(V_H - V_L)/V_L - V_L = K$ during the high reference timing periods $T_H$. Those signals are applied to one input of the differential amplifier 56 the output of which is received by both the sample and hold circuit 57, and the calibration circuit 35.

The circuit 57 samples and holds the output of the differential amplifier 56 during the high reference sampling periods produced by positive periods of the waveform f. Those periods correspond to periods in which the output of the divider 54 is equal to K. Thus, the output of the sample and hold circuit 57 is a signal equal to the multiplier constant voltage K. That voltage is applied to the other input of the differential amplifier 56 via the contacts 58 that are closed during negative or low portions of the waveform f. The final output of the differential amplifier 56, therefore, is equal to K during the high reference sampling periods $S_H$ and is equal to K $(V_S - V_L)/(V_H - V_L) - K$ during the sensing periods $T_S$. The subtraction of K from the desired signal ratio $K(V_S - V_L)/(V_H - V_L)$ reduces the multiplier offset introduced by the divider circuit 56.

After calibration in the calibration circuit 35 the desired ratio signal is applied to the sample and hold circuit 36 (FIG. 1). The circuit 36 samples and holds that signal output during sensor sampling periods $S_S$ that are produced by positive portions of a waveform d (FIG. 9) provided by the timing circuit 23. Again, the sensor sampling periods $S_S$ are shorter and time centered with respect to the sensing periods $T_S$. The provision of shortened, time centered sampling periods $S_S$, $S_H$, and $S_L$ ensures the pertinence of the signal data being processed. After processing, the final outputs of the output circuit 37 are compensated ratio signals indicative of the moisture content of the material 31.

Obviously, many modifications and variations of the present invention are possible in light of the above teachings. For example, although mechanical switching contacts are illustrated to simplify a description of the system 11 it will be understood that the described switching operations are preferably performed by conventional electronic switching techniques. Also, although the illustrated planar electrodes 25, 27 are preferred because they produce greater electric field disturbance and therefore improved sensitivity, it will be obvious that other types of electrodes including open frame parallel and the pulley types could be employed. It is to be understood, therefore, that the invention can be practiced otherwise than as specifically described.

What is claimed is:

1. A moisture analyzing system comprising:
   a frequency-modulated voltage source;
   an antenna means coupled to said source and arranged to apply an alternating electric field to a material being tested for moisture content;
   an LC tank circuit connected in parallel with said antenna means;
   a resistance means connected between said source and said parallel combination of said antenna means and said tank circuit; and
   measurement circuit means detecting the level of resonant voltage peak output signals $V_O$ produced by said tank circuit and providing therewith sensing signals $V_S$ indicative of the moisture content of the material being tested.

2. A system according to claim 1 including reference means producing a high voltage reference signal $V_H$ and a low voltage reference signal $V_L$ less than said high voltage reference signal $V_H$, and wherein said measurement circuit means comprises processing circuit means providing a moisture indicating compensated output signal proportional to $(V_S - V_L)/(V_H - V_L)$.

3. A system according to claim 1 including material feed means for feeding the material through said alternating electric field.

4. A system according to claim 1 wherein said frequency modulated source means comprises a sweep generator and a variable frequency oscillator driven thereby.

5. A system according to claim 4 wherein said antenna means comprises spaced apart planar electrodes adapted to lie on one side of the material and to provide said alternating electric field in a path which twice passes through the material.

6. A system according to claim 2 wherein said reference means comprise a high reference impedance, a low reference impedance; timing means; and switching means responsive to said timing means to maintain said antenna means in parallel with said tank circuit during sensing periods in which said output signal $V_O$ comprises said moisture sensing signal $V_S$, to substitute said high reference impedance for said antenna means during high reference periods when said output signal $V_O$ comprises said high reference signal $V_H$, and to substitute said low reference impedance for said antenna means during low reference periods when said output signal $V_O$ comprises said low reference signal $V_L$.

7. A system according to claim 6 wherein said processing circuit means comprises isolation means responsive to said timing means for separating said output signal $V_O$ into said sensing signal $V_S$, said high reference signal $V_H$, and said low reference signal $V_L$.

8. A system according to claim 7 wherein said high reference impedance comprises capacitor means, and said low reference impedance comprises resistor means.

9. A system according to claim 8 including material feed means for feeding the material through said alternating electric field.

10. A system according to claim 9 wherein said frequency modulated source means comprises a sweep generator and a variable frequency oscillator driven thereby.

11. A system according to claim 7 wherein said sensing periods are substantially longer than either of said high reference or said low reference periods.

12. A system according to claim 11 wherein said timing and switching means are operative to produce between said sensing and said high reference periods first combined periods during which both said antenna means and said high reference impedance are connected in parallel with said tank circuit and to produce between said sensing and said low reference periods second combined periods during which both said antenna means and said low reference impedance are connected in parallel with said tank circuit.

13. A system according to claim 12 wherein said measurement circuit means comprises inverting means for inverting said output signals $V_O$ to produce inverted output signals $\overline{V}_O$, and differential amplifier means receiving said output signals $V_O$ and said inverted output signals $\overline{V}_O$ and producing therewith combined output signals $2V_O$.

14. A system according to claim 7 wherein said processing means comprises detection and storage means for detecting and storing the values of said output signals $V_O$ produced during individual cycles of said frequency modulated source.

15. A system according to claim 14 wherein said storage means comprises storage capacitor means for storing said output signals $V_O$, and said processing circuit further comprises discharge means for discharging said storage capacitor means after each said individual cycle.

16. A system according to claim 14, wherein said processing means further comprises low reference sampling means responsive to said timing means and operative during low reference sampling periods to sample and hold values of said output signal $V_O$ produced during said low reference periods, subtraction circuit means producing a difference signal dependent on the values of $(V_O - V_L)$, high reference sampling means responsive to said timing means and operative during high reference sampling periods to sample and hold values of said difference signals $(V_O - V_L)$ produced during said high reference periods, divider circuit means producing ratio signals dependent on the ratios of said difference signals and the signals stored by said high reference sampling means, and distinguishing circuit means responsive to said timing means and producing from said ratio signals said compensated signal $(V_S - V_L)/(V_H - V_L)$ only during sampling portions of said sensing periods.

17. A system according to claim 16 wherein said low reference sampling periods are shorter than and substantially time centered with respect to said low reference periods, said high reference sampling periods are shorter than and substantially time centered with respect to said high reference periods, and said sampling portions are shorter than and substantially time centered with respect to said sensing periods.

18. A system according to claim 17 wherein said sensing periods are substantially longer than either of said high reference or said low reference periods.

19. A system according to claim 18 wherein said timing and switching means are operative to produce between said sensing and said high reference periods first combined periods during which both said antenna means and said high reference impedance are connected in parallel with said tank circuit, and to produce between said sensing and said low reference periods second combined periods during which both said antenna means and said low reference impedance are connected in parallel with said tank circuit.

20. A system according to claim 19 including material feed means for feeding the material through said alternating electric field.

* * * * *